United States Patent
Birke et al.

(10) Patent No.: US 7,030,056 B2
(45) Date of Patent: Apr. 18, 2006

(54) PROCESS FOR PREPARING A CATALYST, THE CATALYST AND A USE OF THE CATALYST

(75) Inventors: Peter Birke, Leuna (DE); Hans-Dieter Neubauer, Leuna (DE); Rainer Schubert, Leuna (DE)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/395,629

(22) Filed: Mar. 24, 2003

(65) Prior Publication Data

US 2003/0187293 A1    Oct. 2, 2003

(30) Foreign Application Priority Data

Mar. 27, 2002    (EP) .................................. 02006992

(51) Int. Cl.
*B01J 31/00* (2006.01)
*B01J 23/00* (2006.01)

(52) U.S. Cl. ...................... 502/330; 502/333; 502/258; 502/262; 502/325

(58) Field of Classification Search ................ 502/243, 502/330, 333, 258, 262, 325
See application file for complete search history.

(56) References Cited

U.S. PATENT DOCUMENTS

| | | | |
|---|---|---|---|
| 3,743,607 A | 7/1973 | Sennewald | 252/430 |
| 3,822,308 A | 7/1974 | Kronig et al. | 260/497 |
| 4,048,096 A | 9/1977 | Bissot | 252/430 |
| 5,179,056 A | 1/1993 | Bartley | 502/170 |
| 5,179,057 A | 1/1993 | Bartley | 502/170 |
| 5,185,308 A | 2/1993 | Bartley et al. | 502/170 |
| 5,189,004 A | 2/1993 | Bartley | 502/170 |
| 5,225,388 A | 7/1993 | Wunder et al. | 502/170 |
| 5,250,487 A | 10/1993 | Wirtz et al. | 502/243 |
| 5,274,181 A | 12/1993 | Bartley et al. | 560/245 |
| 5,292,931 A | 3/1994 | Wirtz et al. | 560/245 |
| 5,314,858 A | 5/1994 | Colling | 502/330 |
| 5,332,710 A | 7/1994 | Nicolau et al. | 502/243 |
| 5,342,987 A | 8/1994 | Bartley | 560/245 |
| 5,422,329 A | 6/1995 | Wirtz et al. | 502/328 |
| 5,559,071 A | 9/1996 | Abel et al. | 502/326 |
| 5,571,771 A | 11/1996 | Abel et al. | 502/330 |
| 5,674,800 A | 10/1997 | Abel et al. | 502/326 |
| 5,691,267 A * | 11/1997 | Nicolau et al. | 502/330 |
| 5,777,156 A | 7/1998 | Abel et al. | 560/245 |
| 5,854,171 A * | 12/1998 | Nicolau et al. | 502/330 |
| 5,968,860 A | 10/1999 | Herzog | 502/5 |
| 5,972,824 A * | 10/1999 | Herzog et al. | 502/160 |
| 6,015,769 A * | 1/2000 | Wang | 502/331 |
| 6,022,823 A | 2/2000 | Augustine et al. | 502/243 |
| 6,034,030 A | 3/2000 | Nicolau et al. | 502/326 |
| 6,107,513 A | 8/2000 | Herzog et al. | 560/208 |
| 6,114,571 A | 9/2000 | Abel et al. | 560/245 |
| 6,114,573 A | 9/2000 | Herzog | 560/261 |
| 6,207,610 B1 | 3/2001 | Krause et al. | 502/232 |
| 6,303,536 B1 | 10/2001 | Chen et al. | 502/325 |
| 6,303,537 B1 * | 10/2001 | Wang et al. | 502/330 |
| 6,391,821 B1 | 5/2002 | Satoh et al. | 502/300 |
| 6,486,093 B1 * | 11/2002 | Wang et al. | 502/330 |
| 2002/0013220 A1 * | 1/2002 | Wang et al. | 502/171 |

FOREIGN PATENT DOCUMENTS

| | | |
|---|---|---|
| CA | 2018991 | 4/2001 |
| CN | 1250688 | 4/2000 |
| CN | 1268396 | 10/2000 |
| CN | 1297789 | 6/2001 |
| CN | 1297883 | 6/2001 |
| CN | 1340378 | 3/2002 |
| EP | 519435 | 12/1992 |
| EP | 634208 | 1/1995 |
| EP | 634209 | 1/1995 |
| EP | 1106247 | 1/1996 |
| EP | 839793 | 5/1998 |
| EP | 937498 | 8/1999 |
| EP | 965383 | 12/1999 |
| EP | 967009 | 12/1999 |
| EP | 976713 | 2/2000 |
| EP | 985657 | 3/2000 |
| EP | 1006100 | 6/2000 |
| EP | 909213 | 11/2001 |
| EP | 1175939 | 1/2002 |
| EP | 1205246 | 5/2002 |
| GB | 1215210 | 12/1970 |
| GB | 1283737 | 8/1972 |

(Continued)

OTHER PUBLICATIONS

S. Brunauer, P.Y. Emmett and E. Teller, J., Adsorption of Gases in Multimolecular Layers, Am. Chem. Soc. vol. 60, 309-316, publ. Feb. 1938.

(Continued)

*Primary Examiner*—Steven Bos

(57) ABSTRACT

A process for preparing a catalyst which process comprises the steps of:
(a) introducing a Group 8 metal compound onto a carrier,
(b) converting a first portion of the Group 8 metal compound on the carrier into metallic species in a liquid phase reaction, and
(c) subsequently converting a further portion of the Group 8 metal compound on the carrier into metallic species in a gas phase reaction; a catalyst which is obtainable by this process; and a process for preparing an alkenyl carboxylate comprising reacting a mixture comprising an olefin, a carboxylic acid and oxygen in the presence of the catalyst.

22 Claims, No Drawings

FOREIGN PATENT DOCUMENTS

| | | |
|---|---|---|
| WO | 98/18553 | 5/1998 |
| WO | 99/08790 | 2/1999 |
| WO | 99/08791 | 2/1999 |
| WO | 00/15333 | 3/2000 |
| WO | 00/15334 | 3/2000 |
| WO | 00/15335 | 3/2000 |
| WO | 00/58008 | 3/2000 |
| WO | 02/04392 | 1/2002 |
| WO | 99/42212 | 1/2002 |

OTHER PUBLICATIONS

Periodic Table of the Elements as published in R C Weast (Ed,) "Handbook of Chemistry and Physics", 54$^{th}$ edition, CRC Press.

* cited by examiner

PROCESS FOR PREPARING A CATALYST, THE CATALYST AND A USE OF THE CATALYST

FIELD OF THE INVENTION

The invention relates to a process for preparing a catalyst, to a catalyst which is obtainable by the process of this invention, and to a process for preparing an alkenyl carboxylate comprising reacting a mixture comprising an olefin, a carboxylic acid and oxygen in the presence of the catalyst.

BACKGROUND OF THE INVENTION

Catalysts for the preparation of an alkenyl carboxylate from an olefin, a carboxylic acid and oxygen are known in the art. Such catalysts are based on a Group 8 metal as a catalytically active metallic species on a carrier. In preferred embodiments the metallic species further comprise a Group 1b metal. The preparation of the catalysts is well documented.

For example, the process for preparing the catalyst of U.S. Pat. No. 4,048,096 comprises the steps of introducing a Group 8 metal compound onto a carrier and converting the Group 8 metal compound on the carrier into metallic species. The conversion of the Group 8 metal compound may be accomplished in a liquid phase reaction, whereby a reducing agent such as hydrazine or formaldehyde is added to liquid which comprises the Group 8 metal/carrier composition. Alternatively, the conversion of the Group 8 metal compound may be accomplished in a gas phase reaction, whereby a reducing agent such as hydrogen or ethylene is reacted with the Group 8 metal/carrier composition.

The process for preparing the catalyst as disclosed in U.S. Pat. No. 4,048,096 is not without problems. Complete conversion of the Group 8 metal compound on the carrier into metallic species requires typically the presence of a large excess of the reducing agent. This is in particular the case in the liquid phase reaction, and more in particular when the reducing agent has a tendency to decompose under the prevailing reaction conditions, so that a portion of it becomes ineffective in the reduction. After the reduction, any unconverted reducing agent needs to be handled and discarded in an appropriate manner, which may be particularly cumbersome in association with the liquid phase reaction or when the reducing agent is a noxious chemical, such as hydrazine. Further, there is undesirably a loss of the Group 8 metal or Group 8 metal compound occurring during the preparation, which leads to a reduced yield of the Group 8 metal on the catalyst and to increased costs. This is in particular the case when a gas phase reaction is applied.

SUMMARY OF THE INVENTION

The present invention provides a process for preparing a catalyst which process comprises the steps of:
(a) introducing a Group 8 metal compound onto a carrier,
(b) converting a first portion of the Group 8 metal compound on the carrier into metallic species in a liquid phase reaction, and
(c) subsequently converting a further portion of the Group 8 metal compound on the carrier into metallic species in a gas phase reaction.

The invention also provides a catalyst which is obtainable by a process for preparing a catalyst according to this invention.

The invention also provides a process for preparing an alkenyl carboxylate comprising reacting a mixture comprising an olefin, a carboxylic acid and oxygen in the presence of the catalyst of this invention.

DETAILED DESCRIPTION OF THE INVENTION

In accordance with this invention, it is advantageous to carry out the conversion of the Group 8 metal compound into metallic species by a sequential method, which involves the combination of a liquid phase reaction and a gas phase reaction. Applying the sequential method is advantageous as problems are avoided which are associated with the disposal of unconverted reagent from the liquid phase reaction, while the sequential method also minimizes losses of Group 8 metal and Group 1b metal (if present) and therefore leads to a high yield of metallic species on the catalyst.

It is also an unexpected benefit that by applying the combination of a liquid phase reaction and a gas phase reaction instead of applying the liquid phase reaction only, there is an improvement in the dispersity of the metallic species in the catalyst, as measured by an increased carbon monoxide chemisorption of the catalyst. It is theorized that a better dispersity of the metallic species leads to an improved catalyst performance. By the term "improved catalyst performance" it is meant that there is an improvement in at least one of the catalyst properties, which catalyst properties include catalyst activity, selectivity, activity or selectivity performance over time, operability (i.e. resistance to run-away), conversion and work rate. By "selectivity" it is meant the selectivity to alkenyl carboxylate, based on the quantity of olefin converted.

The skilled person will understand that the carrier is generally a solid material and that, therefore, by the term "liquid phase reaction" is meant a reaction which involves contacting the Group 8 metal/carrier composition with a reactive agent (e.g. reducing agent) present in a liquid phase. Likewise, by the term "gas phase reaction" is meant a reaction which involves contacting the Group 8 metal/carrier composition with a reactive agent (e.g. reducing agent) present in a gas phase, in the absence of a continuous liquid phase, preferably in the absence of a liquid phase.

The term "Group 8 metal/carrier composition", as used herein, refers to any composition comprising the carrier and a Group 8 metal dispersed on the carrier, irrespective of whether the Group 8 metal is present as a Group 8 metal compound or Group 8 metal compound precursor, or in the form of metallic species.

The carrier for use in this invention may be of any kind. For example, the carrier may comprise silica, alumina, magnesia, zirconia, fuller's earth, artificial and natural zeolites, and combinations thereof. The carrier is preferably a silica-containing carrier. Such silica-containing carrier may or may not comprise alumina. The silica content of the carrier is typically at least 50% w, more typically at least 90% w, based on the weight of the carrier. Frequently the silica content of the carrier is at most 99.99% w, more frequently at most 99.9% w, on the same basis.

Typically, the carrier is a porous carrier, preferably having a specific surface area of at least $0.01 \text{ m}^2/\text{g}$, in particular in the range of from 0.05 to $1000 \text{ m}^2/\text{g}$, more in particular in the range of from 0.2 to $1000 \text{ m}^2/\text{g}$, as measured by the B.E.T. method, and a water absorption capacity of from 0.05 to 3 ml/g, in particular from 0.1 to 2 ml/g, as measured by conventional water absorption technique. The B.E.T.

method as referred to herein has been described in detail in S. Brunauer, P. Y. Emmett and E. Teller, J. Am. Chem. Soc. 60, 309–16 (1938).

Of particular interest are silicas which have a specific surface area in the range of from 10 to 1000 m$^2$/g, in particular from 50 to 500 m$^2$/g, as measured by the B.E.T. method.

Regardless of the carrier used, it may be shaped into particles, chunks, pieces, and the like. Preferably, for use in a tubular fixed bed reactor, they are formed into a rounded shape, for example in the form of spheres, pellets, cylinders, rings or tablets, typically having dimensions in the range of from 2 mm to 2 cm.

For use in this invention, the carrier is preferably subjected to a series of washings with one or more aqueous liquids. A series of washings is herein understood to include a single washing step and a combination of consecutive washing steps which employ one or more washing liquids. The washing liquids are typically aqueous liquids which all have a pH of at least 3, when measured at 20° C. One skilled in the art will appreciate that aqueous liquids may contain a small quantity of acid, such as resulting from dissolution of atmospheric carbon dioxide, and they may therefore have a pH slightly below 7, for example down to a pH of 3. Such aqueous liquids contain very little acid or the acid is a weak acid, so that yet they are considered to be essentially non-acidic aqueous liquids.

Preferably, the aqueous liquids have all a pH of at least 5, in particular at least 6, more in particular at least 7, when measured at 20° C. Typically, the washing liquids have all a pH of at most 10, in particular at most 9, more in particular at most 8, when measured at 20° C.

As used herein, the term "pH" refers to the pH of an aqueous liquid as measured by using a conventional pH measuring probe which is calibrated by using buffer solutions.

Eligibly, the aqueous liquids comprise for the greater part water, and they may or may not comprise relatively small quantities of other components, for example organic materials, for example esters, ethers, alcohols or ketones, or salts, for example acetates, carbonates, nitrates and oxalates, in particular such salts as lithium, sodium, potassium, ammonium, monoalkylammonium, dialkylammonium, trialkylammonium and tetraalkylammonium salts. Such other components may not be detrimental to the preparation of the catalyst or to the performance of the catalyst when used in the preparation of alkenyl carboxylates. Otherwise, such other components, when left behind on the carrier after the washing may be removed from the carrier, for example by further washing the carrier, by evaporation or by decomposition (i.e. by calcination).

Not wishing to be bound by theory it is believed that as a result of the washing ionizable species are removed from the carrier, or at least from the carrier surface, which ionizable species have an influence on the precipitation and/or the conversion into metallic species, such that the morphology of the active surface of the catalyst is changed to an extent which favours the catalyst performance in the preparation of alkenyl carboxylates. It is believed that the following ionizable species may be associated with these effects: silicates, aluminosilicates, sulphates, chlorides, sodium salts, aluminium salts, calcium salts, magnesium salts, and the like.

The aqueous liquids which comprise a salt as specified hereinbefore may be called ion exchange solutions. The presence of salts in the aqueous liquids may facilitate the removal of ionizable species which are firmly bound to the carrier, so that a desirable result may be achieved in a shorter time or at a lower temperature.

Suitably, the ion exchange solution comprises the salt in a quantity of at most 0.1 moles/l. Suitably, the ion exchange solution comprises the salt in a quantity of at least 0.001 moles/l. Preferably, the ion exchange solution comprises the salt in a quantity in the range of from 0.002 to 0.05 moles/l. The remainder of the solution may be a de-ionized liquid as specified hereinafter.

The water content of the aqueous liquids, in particular when they do not comprise added salt as to form an ion exchange solution, is preferably at least 90% w, more preferably at least 99% w, in particular at least 99.9% w, more in particular at least 99.99% w, relative to the weight of the aqueous liquid. Frequently, the content of water is at most 99.999% w, on the same basis. Preferably, the aqueous liquid is water.

Suitably, the aqueous liquids have a low conductivity. Such low-conductivity aqueous liquids typically do not comprise added salt as to form an ion exchange solution. Suitably, the conductivity is at most 500 µmho (mho is $\Omega^{-1}$, or siemens, or S), more suitably at most 100 µmho, preferably at most 20 µmho, in particular at most 5 µmho, when measured at 98° C. Frequently the conductivity will be at least 0.1 µmho, more frequently at least 0.2 µmho, on the same basis. Conductivities are herein understood to be electrical conductivities, measured by using a conductivity measuring probe having a cell constant of 1.0/cm. Suitably a YSI Model 3401 (trademark) conductivity measuring probe is used, connected to a YSI Model 35 (trade mark) conductance meter. Such low-conductivity aqueous liquids are typically de-ionized aqueous liquids. The de-ionized aqueous liquids are obtainable by de-ionisation using an ion exchange material such as an ion exchange resin, typically a cation exchange material in the acidic form, or an anion exchange material in the basic form, but preferably using a cation exchange material in the acidic (H$^+$) form and an anion exchange material in the basic (OH$^-$) form.

The washing may be carried out in a continuous fashion or it may be a batch type operation. There may be one washing, but the number of washings may also be two, or three, or more, for example up to five or ten. The quantity of aqueous liquid used in the washings relative to the quantity of the carrier is not material to the invention. The washing may be carried out a temperature in the range of from 10 to 300° C., preferably at a temperature in the range of from 50 to 150° C., for example about 100° C. However, when using an ion exchange solution, the temperature is preferably in the range of from 20 to 120° C., for example about 70° C.

The washing may be monitored by applying a conductivity test, which conductivity test involves contacting samples of water with samples of the carrier, unwashed and washed, and measuring the conductivity of each water sample after it has reached equilibrium with the respective carrier sample at 95° C. In this conductivity test the conductivity is measured at 95° C., the quantity of water sample is 3 g/g carrier sample and the conductivity of the water prior to the contacting with the carrier sample is 1.5 µmho at 98° C. Water eligible for use in the conductivity test is water which is de-ionized using a cation exchange material in the H$^+$ form and an anion exchange material in the OH$^-$ form.

Typically the carrier is washed to the extent that in the conductivity test the conductivity measured for the washed carrier is less than 50% of the value found for the unwashed catalyst, preferably less than 30%, more preferably less than 20%. Frequently, the carrier is washed to the extent that in the conductivity test the measured conductivity is at least 1%, more frequently at least 5% of the value found for the unwashed catalyst.

Typically the carrier is washed to the extent that in the conductivity test the conductivity measured for the washed carrier is less than 200 μmho, more typically less than 75 μmho, preferably less than 50 μmho. The carrier may be washed such as to achieve that the conductivity measured in the conductivity test is as low as possible. However, in practice the carrier may be washed to the extent that the conductivity measured in the conductivity test is above 2 μmho, more frequently above 3 μmho.

As an alternative to, or in addition to washing the carrier, one or more materials from which the carrier is formed may be subjected to a series of washings as, and to the extent, described hereinbefore. Subsequently, the carrier may be formed from the materials by conventional mixing and/or shaping methods, such as extrusion.

The Group 8 metal for use in this invention has suitably an atomic number of at least 44 and at most 78. One or more Group 8 metals may be applied. Preferably, the Group 8 metal is palladium.

Preferably, the catalyst is based on a Group 1b metal, in addition to a Group 8 metal. One or more Group 1b metals may be applied. The Group 1b metal is preferably gold.

The terms "Group 8 metal" and "Group 1b metal" as used herein refer to the metals of Group 8 and Group 1b, respectively, of the Periodic Table of the Elements as published in R C Weast (Ed.) "Handbook of Chemistry and Physics", 54$^{th}$ edition, CRC Press, inside cover.

In a preferred embodiment, the catalyst is based on palladium as the Group 8 metal and gold as the Group 1b metal.

Suitably the Group 8 metal compound and optionally the Group 1b metal compound is introduced onto the carrier by pore impregnating the carrier with one or more aqueous solutions comprising a Group 8 metal compound precursor and optionally a Group 1b metal compound precursor and, in preferred embodiments, then precipitating the Group 8 metal compound and optionally the Group 1b metal compound onto the carrier from such solutions, by using a precipitating agent. In more detail, the applicable materials and methods may be those as disclosed in U.S. Pat. Nos. 4,048,096, 5,179,057 and 5,189,004, which are incorporated herein by reference.

In other embodiments of this invention, the Group 8 metal compound precursor and optionally the Group 1b metal compound precursor may be introduced onto the carrier, following for example procedures as disclosed in WO-99/08790 and WO-99/08791, and thereafter converted into metallic species in accordance with the present invention. This means that in the catalyst preparation according to this invention the Group 8 metal compound precursor and the Group 1b metal compound precursor, if present, may be converted into metallic species and simultaneously precipitated.

The volume of an impregnation solution preferably corresponds to at least 80%, preferably 95 to 100% of the water absorption capacity of the carrier.

Eligible Group 8 metal compound precursors and Group 1b metal compound precursors are for example water soluble acids and salts, such as chlorides, nitrates, nitrites and sulphates. Preferred such Group 8 containing acids and salts are palladium (II) chloride, palladium (II) nitrate, and palladium (II) sulphate and, in particular, sodium palladium (II) tetrachloride. Preferred such Group 1b metal containing acids and salts are auric (III) chloride and, in particular, tetrachloroauric (III) acid.

The precipitating agent includes for example alkali metal hydroxides, alkali metal bicarbonates, alkali metal carbonates and, preferably, alkali metal silicates. Suitable alkali metals are lithium, sodium and potassium. The preferred precipitating agent is sodium silicate. A useful form of sodium silicate is sodium metasilicate pentahydrate. The precipitating agent is suitably used in an excess relative to the Group 8 metal and optionally the Group 1b metal, taken together. For example, the precipitating agent may be used in a quantity of 1 to 3 moles, preferably 1.5 to 2.5 moles per mole of Group 8 metal compound precursor. If the Group 1b metal precursor is present, an additional quantity of the precipitating agent may be used, for example 2 to 10 moles, preferably 2.5 to 8 moles per mole of Group 1b metal compound precursor.

The precipitating agent is preferably used as an aqueous solution. The aqueous solution has typically a volume sufficient to cover the impregnated, wet carrier particles. As an alternative, after the impregnation with one or more solutions comprising a Group 8 metal compound precursor and optionally a Group 1b metal compound precursor, the carrier particles may be dried and subsequently impregnated with an aqueous solution comprising the precipitating agent. In the latter case, the volume of the aqueous solution of the precipitating agent typically corresponds to at least 80%, preferably 95 to 100% of the water absorption capacity of the carrier.

The temperature at which the precipitation may be carried out is typically in the range of from 1 to 100° C., more typically in the range of from 5 to 50° C., for example about 20° C. The reaction time applied in the precipitation step may be for example at least 2 hours, more preferably at least 3 hours, and it may be for example up to 100 hours, more typically it is in the range of from 6 to 40 hours, for example 24 hours. During the precipitation, the particles may be left static, or they may be moved relative to the solution of the precipitation agent, or relative to each other. For example, the particles may be moved relatively to each other, for example by shaking, during the initial stages of the precipitation, for example during the first 15 minutes, or first 30 minutes, or first hour. Upon completion of the precipitation, the pH of the precipitating solution is preferably in the range of from 6.5 to 11, for example 6.5 to 9.5, but more preferably it is in the range of from 7.5 to 10, in particular from 7.5 to 8, when measured at 20° C. The final pH may be adjusted by changing the quantity of the precipitating agent.

The quantity of the Group 8 metal compound precursor may be such that in the catalyst as prepared the content of the Group 8 metal is typically in the range of from 10 to 500 mmoles/kg catalyst, and preferably in the range of from 20 to 200 mmoles/kg catalyst, for example about 75 mmoles/kg or about 138 mmoles/kg.

The quantity of the Group 1b metal compound precursor may be such that in the catalyst as prepared the content of the Group 1b metal is typically in the range of from 1 to 200 mmoles/kg catalyst, and preferably in the range of from 5 to 100 mmoles/kg catalyst, for example about 37.2 mmoles/kg or about 65 mmoles/kg.

In accordance with this invention, a first portion of the Group 8 metal compound and, if present, the Group 1b metal compound on the carrier is converted into metallic species in a liquid phase reaction. Subsequently, a further portion of the Group 8 metal compound and, if present, the Group 1b metal compound on the carrier is converted into metallic species in a gas phase reaction.

If the Group 8 metal in the Group 8 metal compound and, if present, the Group 1b metal in the Group 1b metal compound are not in their zero valence state, the conversion into metallic species may be accomplished by reduction. Suitable reducing agents and reduction methods are known from U.S. Pat. Nos. 4,048,096, 5,179,057 and 5,189,004, which are incorporated herein by reference.

Typically, the reducing agent for use in the liquid phase reaction (hereinafter, "the first reducing agent") is selected from the non-gaseous reduction agents, i.e. the reducing agents which, as a pure material, can exist at the prevailing reaction temperature, in particular at 20° C., in liquid or solid state. This assists in preventing that gas bubbles are present in the liquid phase reaction.

The liquid phase may be non-aqueous, for example alcoholic or hydrocarbonaceous, but preferably it is aqueous. The liquid phase may comprise other compounds than the first reducing agent, for example an excess of the precipitation agent and reaction products of the precipitation reaction which do not comprise species of the Group 8 metal or, if present, the Group 1b metal. The first reducing agent is preferably soluble in, or miscible with the liquid phase, in particular the aqueous liquid phase. Preferred first reducing agents are selected from diborane; amines, for example ammonia and hydrazine; carboxylic acids and their salts, for example oxalic acid, potassium oxalate, formic acid, potassium formate, ammonium citrate; aldehydes, for example formaldehyde, acetaldehyde; hydrogen peroxide; reducing sugars for example glucose; polyhydric phenols, for example hydroquinone and catechol; or sodium borohydride. The preferred first reducing agent is hydrazine.

The first reducing agent is typically employed in a quantity such that a major quantity of the Group 8 metal compound and, if present, the Group 1b metal compound on the carrier will be reduced. When the first reducing agent does not have a tendency to decompose under the prevailing reaction conditions, this may be achieved by employing a stoichiometric quantity, or less, of the first reducing agent, relative to the total of the Group 8 metal and the Group 1b metal, if present, and allowing the first reducing agent to completely react away. For example, the quantity of the first reducing agent may be at least 50%, preferably in the range of from 70 to 99%, more preferably in the range of from 80 to 90% of the stoichiometric quantity. When the first reducing agent has a tendency to decompose under the prevailing reaction conditions, larger quantities, for example larger than a stoichiometric quantity, may be needed to accomplish the same result. For example, when the first reducing agent is hydrazine, the quantity may typically be in the range of from 0.5 to 10 times, more typically from 0.8 to 8 times, in particular from 1 to 5 times, the stoichiometric quantity may be employed. The major quantity of the Group 8 metal compound and, if present, the Group 1b metal compound may represent at least 50%-mole, preferably at least 70%-mole, more preferably at least 80%-mole, relative to the total of the Group 8 metal and Group 1b metal, if present. The major quantity of the Group 8 metal compound and, if present, the Group 1b metal compound may represent preferably at most 99%-mole, more preferably at most 90%-mole, relative to the total of the Group 8 metal and Group 1b metal, if present. The major quantity of the Group 8 metal compound and, if present, the Group 1b metal compound may represent preferably from 70 to 99%-mole, more preferably from 80 to 90%-mole, relative to the total of the Group 8 metal and Group 1b metal, if present.

The temperature which may be employed in the liquid phase reaction, in particular when hydrazine is employed in an aqueous diluent, is typically in the range of from 0 to 100° C., more typically from 5 to 50° C., for example 20° C. or ambient temperature. The pressure may be selected within wide ranges, for example between 10 and 1000 kPa, more typically between 50 and 200 kPa. Preferably, the pressure is the ambient pressure. The reaction time involved in reacting away the first reducing agent may typically amount to 0.5 to 10 hours, more typically 1 to 5 hours, for example 4 to 5 hours.

After a first portion of the Group 8 metal compound and, if present, the Group 1b metal compound on the carrier has been converted into metallic species in the liquid phase reaction, the Group 8 metal/carrier composition may be subjected to a purification step (c), wherein the Group 8 metal/carrier composition is freed from unwanted reaction products, for example from the precipitation step and the reduction.

The purification treatment suitably involves a series of washings of the Group 8 metal/carrier composition, with one or more aqueous liquids. Eligibly, the aqueous liquids for use in the purification treatment may be selected from the aqueous liquids as specified hereinbefore for the washing of the carrier. The purification treatment may be carried out at a temperature in the range of from 0 to 100° C., preferably at a temperature in the range of from 5 to 50° C., for example about 20° C.

The purification treatment may be monitored by any suitable means, for example by applying the conductivity test as described hereinbefore. Alternatively, the purification treatment may be monitored by following the disappearance of contaminants which are to be removed, such as sodium ions or chloride, in accordance with the nature of, for example, the Group 8 metal compound precursor, the precipitating agent and the reducing agent. In this respect, reference may be made to U.S. Pat. Nos. 4,048,096, 5,179,057 and 5,189,004, which are incorporated herein by reference.

The Group 8 metal/carrier composition may be freed from liquid by mechanical separation, for example filtration or centrifugation, and evaporation of liquid, i.e. by a drying step, or by any combination of mechanical separation and evaporation. Such drying is typically performed at a temperature in the range of from 50 to 300° C., more typically in the range of from 80 to 150° C., for example 90° C., or 115° C., or 120° C., using an inert gas, such as nitrogen or helium, or air.

It is preferred to free the composition from liquid as it brings the Group 8 metal/carrier composition in a form wherein it is more suitable for the conversion of the further portion of the Group 8 metal compound and, if present, the Group 1b metal compound on the carrier into metallic species in a gas phase reaction.

Typically, the reducing agent for use in the gas phase reaction (hereinafter, "the second reducing agent") is a gaseous reducing agent, i.e. a reducing agent which, as a pure material, does not exist in liquid or solid state at the prevailing reaction conditions, in particular at 20° C. and 100 kPa. This assists in preventing the formation of a liquid phase or an additional solid phase in the gas phase reaction.

The second reducing agents may suitably be selected from hydrogen; carbon monoxide; alcohols, for example methanol and ethanol; aldehydes, for example formaldehyde and acetaldehyde; and olefins, such as ethylene, propene and isobutene. The preferred second reducing agent is hydrogen.

Gaseous compounds other than the second reducing agent may be added to the gas phase, for example as a diluent. Such other gaseous compounds are for example helium, argon and nitrogen.

In the gas phase reaction, in particular when hydrogen is employed, the pressure is typically in the range of from 50 to 2000 kPa, more typically from 100 to 1000 kPa, and typically the temperature is in the range of from 10 to 300° C., more typically from 50 to 250° C. When hydrogen is present, the hydrogen partial pressure is typically in the range of from 1 to 2000 kPa.

The gas phase reaction is typically carried out in such a way that the Group 8 metal compound and, if present, the Group 1b metal compound on the carrier are completely converted into metallic species. The reaction time to achieve complete conversion into metallic species is typically at least 0.25 hours, typically in the range of from 0.5 to 5 hours.

The present process for preparing a catalyst may comprise in addition the step of impregnating with a source of an alkali metal, such as disclosed in U.S. Pat. Nos. 4,048,096, 5,179,057 and 5,189,004, which are herein incorporated by reference. Any source of an alkali metal may be used such that the alkali metal deposited on the Group 8 metal/carrier composition can form an alkali metal carboxylate or maintain the presence of an alkali metal carboxylate upon contact with an carboxylic acid, such as during the subsequent use of the catalyst in the preparation of an alkenyl carboxylate.

Suitable sources of an alkali metal are for example alkali metal carbonates and, preferably, alkali metal carboxylates. The alkali metal carboxylate is typically derived from a mono carboxylic acid, such as butyric acid, propionic acid and, preferably, acetic acid. The alkali metal may be any one or more of lithium, sodium, potassium, rubidium and cesium. Preferably, the alkali metal is potassium. The preferred alkali metal carboxylate is potassium acetate. The quantity of the alkali metal carboxylate is typically such that the alkali metal content of the catalyst is in the range of from 0.1 to 5 mole/kg, more preferably from 0.2 to 2 mole/kg catalyst, for example 340 mmole/kg, or 585 mmole/kg, or 765 mmole/kg, or 1560 mmole/kg.

The step of impregnating with an alkali metal carboxylate may be carried out at any stage of the catalyst preparation. Preferably, the Group 8 metal/carrier composition is impregnated with an alkali metal carboxylate after the conversion of the further portion of the Group 8 metal compound and, if present, the Group 1b metal compound on the carrier into metallic species in a gas phase reaction.

The step of impregnating with an alkali metal carboxylate is suitably followed by a drying step, as described hereinbefore.

Preferably, the last step in the catalyst preparation in which liquids are involved is a drying step, after which the catalyst may or may not be subjected to essentially dry operations, such as milling and sieving.

The catalyst which is prepared by the methods described hereinbefore is typically a shell type catalyst, i.e. a catalyst which comprises the catalytically active species, viz. the Group 8 metallic species and the Group 1b metallic species, in the surface layer of the carrier. For example, 90%-mole of the Group 8 metallic species may be distributed within the surface layer extending at most 2 mm from the surface of the carrier. In more preferred embodiments, 90%-mole of the Group 8 metallic species may be distributed within the surface layer extending at most 1.5 mm, in particular at most 1 mm, from the surface of the carrier. Frequently the surface layer in question extends at least 0.05 mm, in particular at least 0.1 mm, from the surface of the carrier.

The present process for preparing an alkenyl carboxylate comprises reacting a mixture comprising an olefin, a carboxylic acid and oxygen in the presence of the catalyst of this invention. The process is frequently a gas phase process, wherein a gaseous feed comprising the reactants is contacted with the solid catalyst. The catalyst is suitably present in the form of a fluidized bed of catalyst particles, or, more suitably, in the form of a packed bed. The process may be carried out as a batch process, however it is more suitable to carry out the process as a continuous process.

The carboxylic acid is preferably a monocarboxylic acid, for example butyric acid, propionic acid, or preferably acetic acid.

The olefin is typically a monoolefin, for example 1-butene, 2-butene, isobutene, propylene, or preferably ethylene.

Most preferably, the carboxylic acid is acetic acid and the olefin is ethylene, in which case the alkenyl carboxylate is vinyl acetate.

The quantity of carboxylic acid is suitably in the range of from 1 to 20%-mole, more suitably in the range of from 5 to 15%-mole, relative to the number of moles of the feed. The quantity of olefin is suitably in the range of from 10 to 80%-mole, more suitably in the range of from 30 to 60%-mole, relative to the number of moles of the feed. The quantity of oxygen is suitably in the range of from 1 to 15%-mole, more suitably in the range of from 5 to 10%-mole, relative to the number of moles of the feed. One skilled in the art will understand that for a gaseous feed a mole fraction corresponds with a volume fraction.

The source of oxygen may be air. Air may be used in the process of this invention, but it is preferred that an oxygen-containing gas which may be obtained by separation from air is used.

Furthermore, inert compounds may be present in the mixture, for example methane, ethane, carbon dioxide, nitrogen or argon. Inert compounds may typically be present in a quantity of from 5 to 80%-mole, more typically from 10 to 60%-mole, relative to the number of moles of the feed.

The process may preferably be carried out at a temperature in the range of from 100 to 250° C., in particular in the range of from 130 to 200° C. As time proceeds, the temperature may be increased gradually, as to compensate for loss in activity of the catalyst, if any. The process may preferably be carried out at a pressure in the range of from 100 to 2500 kPa, in particular in the range of from 200 to 2000 kPa.

In general, it is preferred to operate at a high oxygen concentration. However, in actual practice in order to remain outside the flammability limits of the reactor streams, the concentration of oxygen has to be lowered as the concentration of the olefin and/or oxygenate is increased. The actual safe operating conditions depend along with the gas composition, also on individual plant conditions, such as temperature and pressure. Therefore, for each individual plant the concentration of oxygen will be determined which may be used with any concentration of the olefin and the oxygenate.

When operating the process as a gas phase process using a packed bed reactor, the GHSV may preferably be in the range of from 1000 to 10000 Nl/(l.h). The term "GHSV" stands for the Gas Hourly Space Velocity, which is the volumetric flow rate of the feed, which is herein defined at normal conditions (i.e. 0° C. and 100 kPa), divided by the volume of the catalyst bed.

The alkenyl carboxylate may be recovered from the reaction product by known means, such as by fractional distillation or reactive distillation.

Unless specified otherwise, the organic compounds mentioned herein have typically at most 10 carbon atoms, in particular at most 6 carbon atoms. Organic compounds are deemed to be compounds which comprise carbon atoms and hydrogen atoms and carbon-hydrogen bonds in their molecules.

It is apparent that certain features of the invention, which are for clarity described herein in the context of separate embodiments, may also be provided in combination in a single embodiment. Conversely, features of the invention which are described in the context of a single embodiment may also be provided separately or in any suitable subcombination.

The invention will be illustrated by means of the following, non-limiting examples.

EXAMPLE 1

A 500 g sample of a silica spheres carrier (spheres diameter 5 mm, surface area 137 m$^2$/g, water absorption capacity 0.63 ml/g, obtained from Südchemie, under the trademark KA-160) was washed by immersing the carrier in boiling de-ionized water (6 kg, having a conductivity of 1.5 μmho at 98° C.) in a continuously replenishing vessel (flow rate 0.76 l/min). The conductivity of the washing water was measured continuously at 95° C. After 12 minutes the peak value of the conductivity was 60 μmho and after 120 minutes the conductivity was 6 μmho, at which point the carrier was subjected to drying at about 120° C. for 15 hours in air, and cooled.

A catalyst was then prepared from the washed and dried carrier by applying the following steps:

1. A 25 g sample of the washed carrier was impregnated with 15.7 ml of a solution of sodium palladium (II) tetrachloride (Na$_2$PdCl$_4$) and tetrachloroauric (III) acid (HAuCl$_4$) in de-ionized water containing 0.220 g palladium and 0.121 g gold. A container holding the carrier was gently shaken to allow solution uptake by the carrier. After complete uptake of the solution the impregnated carrier was allowed to stand for 2 hours at room temperature.
2. Then 30 ml of a solution containing 1.68 g sodium metasilicate pentahydrate (Na$_2$SiO$_3$.5H$_2$O) was added to completely cover the wet impregnated support. This was allowed to stand for 15 hours.
3. Subsequently, 2.5 ml of 2.8% w hydrazine hydrate in water was added, mixed gently and allowed to stand for 4 hours at room temperature. This led to the reduction of about 55%-mole of the total of the palladium and gold salts to metallic species.
4. The palladium/carrier composition was then washed with distilled de-ionized water three times by decantation followed by a continuous wash until the wash water was free of chloride, as checked by the absence of a precipitate when tested with a silver nitrate solution. The washed palladium/carrier composition was then dried at about 120° C. for 4 hours under nitrogen, and cooled in a container protected from moisture.
5. The palladium/carrier composition was then subjected to reduction in a hydrogen/nitrogen (15:85 v/v) mixture, at a flow rate of the hydrogen/nitrogen mixture of 500 Nl/(l catalyst.h), at a temperature of 220° C., and at a pressure of 100 kPa, until completion of the reduction, i.e. about 2 hours.
6. The palladium/carrier composition was then impregnated with 15.7 ml of a solution of potassium acetate in de-ionized water containing 1.34 g potassium, dried at about 120° C. for 15 hours under nitrogen, and cooled.

The catalyst thus prepared had a palladium content of 0.75% w, a gold content of 0.4% w and its carbon monoxide chemisorption was 25.3 mmol per kg catalyst.

EXAMPLE 2

Vinyl acetate is prepared as follows.

The catalyst prepared in Example 1 is tested in a reaction tube having a length of 30 cm and an inside diameter of 1.51 cm. The tube is loaded with 2.5 g of catalyst diluted into a 10 cm bed of glass beads. The reaction tube is fed with a gaseous mixture of 49%-mole ethylene, 13%-mole acetic acid and 7.6%-mole oxygen (balance nitrogen). The GHSV is 4250 Nl/(l.h), calculated on undiluted catalyst, and the pressure is 880 kPa (i.e. 7.8 barg). With the catalyst temperature initially at 147° C., vinyl acetate is produced. The jacket temperature is increased slowly so as to keep the space-time-yield constant.

EXAMPLE 3

Example 1 is repeated, with the exception that, in step 3, 2.5 ml of 12% w hydrazine hydrate in water is used instead of 2.5 ml of 2.8% w hydrazine hydrate in water. This leads in this step 3 to the reduction of about 82–85%-mole of the total of the palladium and gold salts to metallic species.

The catalyst so prepared is tested in the preparation of vinyl acetate as described in Example 2.

We claim:

1. A process for preparing a catalyst which process comprises the steps of:
   (a) introducing a Group 8 metal compound onto a carrier,
   (b) converting a first portion of the Group 8 metal compound on the carrier into metallic species in a liquid phase reaction, and
   (c) subsequently converting a further portion of the Group 8 metal compound on the carrier into metallic species in a gas phase reaction.
2. A process as claimed in claim 1, wherein the carrier is a silica-containing carrier.
3. A process as claimed in claim 1, wherein the catalyst is based on palladium as the Group 8 metal, and in addition on a Group 1b metal comprising gold.
4. A process as claimed in claim 1, wherein the Group 8 metal and optionally in addition a Group 1b metal is precipitated onto the carrier by pore impregnating the carrier with one or more aqueous solutions comprising a Group 8 metal compound precursor and optionally a Group 1b metal compound precursor and then precipitating a Group 8 metal compound and optionally a Group 1b metal compound onto the carrier from such solutions, by using a precipitating agent.
5. A process as claimed in claim 1, wherein in the liquid phase reaction at least 50%-mole of the total of the Group 8 metal and an optional Group 1b metal, if any, present on the carrier, is converted into metallic species.
6. A process as claimed in claim 5, wherein in the liquid phase reaction at most 99%-mole of the total of the Group 8 metal and the optional Group 1b metal, if any, present on the carrier, is converted into metallic species.
7. A process as claimed in claim 6, wherein in the liquid phase reaction 70 to 90%-mole of the total of the Group 8 metal and the optional Group 1b metal, if any, present on the carrier, is converted into metallic species.

8. A process as claimed in claim 1, wherein in the liquid phase reaction the Group 8 metal compound on the carrier is converted into metallic species by reaction with a non-gaseous reducing agent.

9. A process as claimed in claim 8, wherein the non-gaseous reducing agent comprises hydrazine.

10. A process as claimed in claim 1, wherein in the gas phase reaction the remaining portion of the Group 8 metal compound on the carrier is converted into metallic species.

11. A process as claimed in claim 1, wherein in the gas phase reaction the Group 8 metal compound on the carrier is converted into metallic species by reaction with a gaseous reducing agent.

12. A process as claimed in claim 11, wherein the gaseous reducing agent comprises hydrogen.

13. A process as claimed in claim 1, which comprises in addition a step of impregnation with a source of an alkali metal.

14. A process as claimed in claim 1, wherein
    (1) the carrier is a silica-containing carrier,
    (2) the catalyst is based on palladium as the Group 8 metal, and in addition on a Group 1b metal comprising gold,
    (3) the Group 8 metal and the Group 1b metal are precipitated onto the carrier by pore impregnating the carrier with one or more aqueous solutions comprising a Group 8 metal compound precursor and a Group 1b metal compound precursor and then precipitating a Group 8 metal compound and a Group 1b metal compound onto the carrier from such solutions, by using a precipitating agent, and
    (4) in the liquid phase reaction at least 50%-mole of the total of the Group 8 metal and the Group 1b metal present on the carrier is converted into metallic species.

15. A process as claimed in claim 14, wherein in the liquid phase reaction 70 to 99%-mole of the total of the Group 8 metal and the Group 1b metal present on the carrier is converted into metallic species.

16. A process as claimed in claim 15, wherein in the liquid phase reaction 80 to 90%-mole of the total of the Group 8 metal and the Group 1b metal present on the carrier is converted into metallic species.

17. A process as claimed in claim 14, wherein in the liquid phase reaction the Group 8 metal compound on the carrier is converted into metallic species by reaction with a non-gaseous reducing agent.

18. A process as claimed in claim 17, wherein the non-gaseous reducing agent comprises hydrazine.

19. A process as claimed in claim 14, wherein in the gas phase reaction the Group 8 metal compound on the carrier is converted into metallic species by reaction with a gaseous reducing agent.

20. A process as claimed in claim 19, wherein the gaseous reducing agent comprises hydrogen.

21. A process for preparing a catalyst which process comprises the steps of:
    (a) introducing a Group 8 metal compound onto a carrier,
    (b) converting a first portion of the Group 8 metal compound on the carrier into metallic species in a liquid phase reaction,
    (c) subsequently converting a further portion of the Group 8 metal compound on the carrier into metallic species in a gas phase reaction, and
    (d) subsequently impregnating with a source of an alkali metal.

22. A process as claimed in claim 21, wherein the alkali metal comprises potassium.

* * * * *